United States Patent [19]

Shibahara et al.

[11] Patent Number: 5,264,213
[45] Date of Patent: Nov. 23, 1993

[54] PROCESS FOR PREPARING HIGHLY ACTIVE WATER-DISPERSIBLE PESTICIDES

[75] Inventors: Tetsuya Shibahara, Hatano; Naohiko Kondo, Atsugi; Jun Kato, Susono, all of Japan

[73] Assignee: DowElanco, Indianapolis, Ind.

[21] Appl. No.: 377,026

[22] Filed: Jul. 7, 1989

[30] Foreign Application Priority Data

Jul. 8, 1988 [JP] Japan .................. 63-168672

[51] Int. Cl.$^5$ .................. C07C 127/22; A01N 9/20
[52] U.S. Cl. .................. 424/409; 514/351; 514/522; 514/594; 546/300; 564/44
[58] Field of Search .......... 546/300; 564/44; 514/351, 522, 554; 424/409

[56] References Cited

U.S. PATENT DOCUMENTS

| | | |
|---|---|---|
| 3,989,842 | 11/1976 | Wellinger et al. |
| 3,989,942 | 11/1976 | Wellinga et al. ........ 424/322 |
| 4,139,636 | 2/1979 | Sirrenberg et al. |
| 4,170,657 | 10/1979 | Rigterink ................ 424/322 |
| 4,262,020 | 4/1981 | Ehrenfreund ........... 514/594 |
| 4,468,405 | 8/1984 | Rigterink et al. |

FOREIGN PATENT DOCUMENTS

| | | |
|---|---|---|
| 2726684 | 6/1977 | Fed. Rep. of Germany. |
| 60-193960 | 12/1984 | Japan. |
| 62-155248 | 7/1987 | Japan. |

OTHER PUBLICATIONS

Nishiyama, et al., Japanese Patent Application 57-145,861, published Sep. 9, 1982 (Derwent Abstract 82-88831 E/42).

Shimazaki, et al., Japanese Patent Application 59-212,462, published Dec. 1, 1984 (Derwent Abstract 85-015809/03).

Haga, et al., Japanese Patent Application 60-193,960, published Oct. 2, 1985 (Derwent Abstract 85-285507/46).

Haga, et al., Japanese Patent Application 62-155,248, published Jul. 10, 1987 (Derwent Abstract 87-231613/33).

Haga, et al., Japanese Patent Application 62-155,249, published Jul. 10, 1987 (Derwent Abstract 87-231614/33).

Nagasaki, et al., Japanese Patent Application 62-195,365, published Aug. 28, 1989 (Derwent Abstract 87-280996/40).

*Primary Examiner*—Lester L. Lee
*Attorney, Agent, or Firm*—D. Wendell Osborne

[57] ABSTRACT

A highly active water-dispersible pesticide formulation is prepared by dissolving at least a part of a benzoyl phenyl urea series insecticidal compound in an organic solvent, contacting the so obtained mixture with a carrier material, and pulverizing the resulting mixture. The pesticidal formulation obtained has higher pesticidal activity than formulations prepared by a conventional dry methods.

13 Claims, No Drawings

PROCESS FOR PREPARING HIGHLY ACTIVE WATER-DISPERSIBLE PESTICIDES

BACKGROUND OF THE INVENTION

The present invention relates to a process for the preparation of highly active water-dispersible pesticide formulations, more particularly, to a process for the preparation of a water-dispersible pesticide formulation comprising as an active ingredient a pesticidal component of the benzoyl phenyl urea series.

Many water-dispersible pesticide formulations comprising as an active ingredient a benzoyl phenyl urea compound, such as diflubenzuron, triflumuron, chlorofluazuron, teflubenzuron or flufenoxuron are known. These conventional water-dispersible pesticide formulations are prepared by adding the active ingredient to a carrier and a surface active agent, and mixing and pulverizing them. At the time of application, such a water-dispersible pesticide is diluted with water to form a suspension to spray on an object.

The conventional water-dispersible pesticide or wettable powder formulations comprising, for example, diflubenzuron, triflumuron, chlorofluazuron, teflubenzuron or flufenoxuron as an active ingredient are defective in that the activity is lower than that of an emulsion. Accordingly, when a conventional water-dispersible pesticide is diluted with water and the resulting suspension is sprayed on an object, in order to attain a high pesticidal effect, it is necessary to spray a large quantity of the suspension, and problems such as environmental pollution and increased costs arise.

SUMMARY OF THE INVENTION

The inventors made research into developing a process for preparing a water-dispersible pesticide having none of the above-mentioned defects, and as a result, found that when a water-dispersible pesticide formulation is prepared by using a part or all of an active ingredient in the form of a solution in an organic solvent, such as acetone or N-methyl-2-pyrrolidone, to mix the active ingredient with a carrier and the like, a formulation having very high pesticidal effect can be obtained.

More specifically, in accordance with the present invention, there is provided a process for preparing a highly active water-dispersible pesticide, which comprises dissolving at least a part of an insecticidally effective benzoyl phenyl urea series compound represented by the following formula:

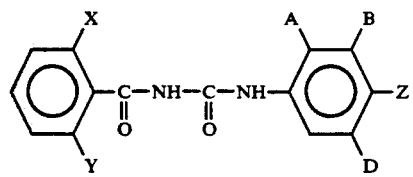

wherein:
X represents Cl, F, Br or $CF_3$;
Y represents H, Cl, F or Br;
Z represents, Cl, F, Br, CN, $CF_3$, $CHF_2$, $OCF_3$, $OCF_2H$, $SCF_3$, $OCF_2CHF_2$, $OCF_2CHFCl$, $OCF_2CHFBr$ or a substituent of the formula

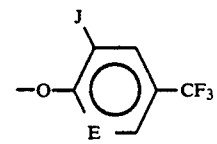

wherein E represents CH or N and J represents H, Cl, F, or Br; and
A, B, and D each independently represent H, $CH_3$, F, Cl or Br in an organic solvent to obtain a mixture comprising a solution containing the pesticidal component, combining the so obtained mixture with a carrier material, and pulverizing combined mixture and carrier material.

DETAILED DESCRIPTION OF THE INVENTION

The benzoyl phenyl urea series compound used in the practice of the present invention is represented by the following formula:

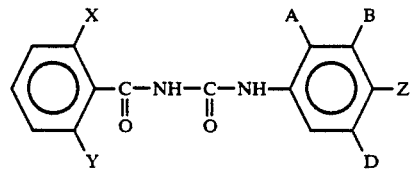

wherein:
X represents Cl, F, Br or $CF_3$;
Y represents H, Cl, F or Br;
Z represents, Cl, F, Br, CN, $CF_3$, $CHF_2$, $OCF_3$, $OCF_2H$, $SCF_3$, $OCF_2CHF_2$, $OCF_2CHFCl$, $OCF_2CHFBr$ or a substituent of the formula

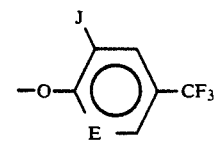

wherein E represents CH or N and J represents H, Cl, F, or Br; and
A, B, and D each independently represent H, $CH_3$, F, Cl or Br.

Suitable examples of the benzoyl phenyl urea series compound used in the present invention include, for example, 1-[3,5-dichloro-4-(1,1,2,2-tetrafluoroethoxy)-phenyl]-3-(2,6-difluorobenzoyl)urea, 1-[3,5-dichloro-4-(3-chloro-5-trifluoromethyl-2-pyridyloxy)phenyl]3-(2,6-difluorobenzoyl)urea (chlorofluazuron), 1-(3,5-dichloro-2-4-difluorophenyl)-3-(2,6-difluorobenzoyl)urea (teflubenzuron), 1-(4-chlorophenyl)-3-(2,6-difluorobenzoyl)urea (diflubenzuron), 1-(4-trifluoromethoxyphenyl)-3-(2-chlorobenzoyl)urea (triflumuron) and 1-[2-fluoro-4-(2-chloro-4-trifluoromethylphenoxy)-phenyl]-3-(2,6-difluorobenzoyl)urea (flufenoxuron) and mixtures thereof.

The organic solvents advantageously used in the present invention include alcohols such as methyl alcohol, ethyl alcohol, isopropyl alcohol and ethylene glycol, ketones such as acetone, methyl ethyl ketone and cyclohexanone, ethers such as dioxane and tetrahydrofuran, aliphatic hydrocarbons such as cyclohexane, solvent naphtha and kerosene, aromatic hydrocarbons such as xylene, trimethylbenzene, tetramethylbenzene, halogenated hydrocarbons such as chloroform, chlorobenzene, tetrachloromethane and dichloromethane, esters such as glycerol esters of fatty acids, nitriles such as acetonitrile, highly polar solvents such as N-methyl-2-pyrrolidone, dimethyl sulfoxide and dimethylformamide and mixtures thereof. In some cases, epoxidized plant oils such as epoxidized soybean oil and epoxidized coconut oil can be used. Examples of preferred solvents include easily volatile solvents such as acetone, dichloromethane, chloroform or methyl alcohol and almost non-volatile solvents such as N-methyl-2-pyrrolidone, cyclohexanone or dimethylformamide. Suitable solvents generally dissolve acylurea insecticides to the extent of at least about five percent and are unreactive toward them. The active ingredient and the solvent are generally mixed in quantities which provide a weight ratio of active ingredient to solvent of from 0.01 to 100, more suitably from 0.05 to 50, most suitably from 0.1 to 10.

After a part or all of the active ingredient has been dissolved in an organic solvent as mentioned above, a surface active agent and a carrier (diluent) are generally added to the solution. Anionic surface active agents of the sulfate and sulfonate types are typically used as the surface active agent. Alternately, a polyoxyethylene type non-ionic surface active agent, a water-soluble polymeric substance or a polyoxyethylene ether phosphate type anionic surface active agent can be used. The sulfate type anionic surface active agents include, for example, alkyl sulfate salts having 12 to 18 carbon atoms, polyoxyethylene $C_{8-12}$ alkyl phenyl ether sulfate salts, polyoxyethylene $C_{12-18}$ ether sulfate salts, and polyoxyethylene/poly-oxypropylene block polymer sulfate salts. In these salts, K, Na, $NH_4$ and aminium salts can be mentioned as the cation. The sulfonate type surface active agents include, for example, dodecylbenzenesulfonates (Na, $NH_4$ and aminium salts), mono- and di-alkyl (having 4 carbon atoms) naphthalenesulfonates (Na and $NH_4$ salts) naphthalenesulfonate (Na salt)/formalin condensates, dialkyl (having 6 to 8 carbon atoms) sulfosuccinates (Na salt), and ligninsulfonates (Na and Ca salts). The non-ionic surface active agents include, for example, polyoxyethylene nonylphenyl ether, polyoxyethylene styryl (or benzyl) phenyl ether, polyoxyethylene sorbitan alkylates, and esters of polyoxyethylene fatty acid having 12 to 18 carbon atoms. As polymeric substances, there can be mentioned polyvinyl alcohol, carboxymethyl cellulose, starch, alginates, and polyacrylic acid salts of Na and amines. Cationic surface active agents and amphoteric surface active agents can be used if desired.

Suitable carriers (diluents) include, for example, plant powders such as soybean powder and wheat flour, mineral powders such as as diatomaceous earth, apatite, gypsum, talc, bentonite, clay, kaolin, calcium carbonate, montmorillonite, feldspar and quartz, and organic and inorganic compounds such as sodium benzoate, urea, Glauber salt, alumina, precipitated silica, (sometimes described as white carbon) and mixtures thereof.

Adjuvants other than the carrier that are customarily used in the field of agricultural chemicals can be appropriately incorporated so as to enhance the pesticidal effect as desired. Examples of such adjuvants include a spreading agent, an emulsifier, a decomposition-prevention agent, a solidification-preventing agent and an activity-increasing agent, such as soybean lecithin. Moreover, another agricultural chemical such as an insecticide, an acaricide, a nematicide, a fungicide, an antiviral agent, an insect attractant, a herbicide and a plant growth regulator, can be used in combination with the active ingredient if desired. An enhanced effect can sometimes be obtained in this case. The amount of the adjuvant or the other agricultural chemical used varies dependent on the kind of adjuvant or agricultural chemical, and can easily be determined by a person skilled in the art.

Examples of the insecticides, acaricides or nematicides advantageously employed include organic phosphoric acid ester compounds such as O-(4-bromo-2-chlorophenyl) O-ethyl S-propyl phosphorothioate, 2,2-dichlorovinyl dimethyl phosphate, ethyl 3-methyl-4-methylthiophenyl isopropylphosphoramidate, O,O-dimethyl O-4-nitro-m-tolyl phosphorothioate, O-ethyl O-4-nitrophenyl phenylphosphonothioate, O,O-diethyl O-2-isopropyl-6-methylpyrimidine-4-yl phosphorothioate, O,O-dimethyl O-(3,5,6-trichloro-2-pyridyl) phosphorothioate, O,S-dimethyl acetylphoroamidothioate and O-(2,4-dichlorophenyl) O-ethyl S-propyl phosphordithioate; carbamate compounds such as 1-naphthyl methylcarbamate, 2-isopropoxyphenyl methylcarbamate, 2-methyl-2-methylthiopropionaldehyde O-methylcarbamoyloxime, 2,3-dihydro-2,2-dimethylbenzofuran-7yl methylcarbamate, dimethyl N,N-(thiobis[-(methylimino)carbonyloxy])ethaneimidothioate, S-methyl-N-(methylcarbamoyloxy) thioacetoimidate, N,N-dimethylcarbamoyloxyimino-2-(methylthio)acetamide, 2-(ethylthiomethyl)phenyl methylcarbamate, 2-dimethylamino-5,6-dimethylpyridin-4-yl dimethylcarbamate and S,S'-2-dimethylaminotrimethylene bisthiocarbamate; organic chlorine compounds such as 2,2,2-trichloro-1,1-bis(4-chlorophenyl)ethanol and 4-chlorophenyl 2,4,5-trichlorophenyl sulfone; organic metal compounds such as tricyclohexyl tin hydroxide; pyrethroid compounds such as (RS)-α-cyano-3-phenoxybenzyl (RS)-2-(4-chlorophenyl)-3-methyl butyrate, 3-phenoxybenzyl (1RS)cis, trans-3-(2,2-dichlorovinyl)-2,2-dimethylcyclopropanecarboxylate, (RS)-α-cyano-3-phenoxybenzyl (1RS)cis,trans-3-(2,2-dichlorovinyl)-2,2-dimethylcyclopropanecarboxylate, (S)-α-cyano-3-phenoxybenzyl (1R)cis-3-(2,2-dibromovinyl)-2,2-dimethylcyclopropanecarboxylate, (RS)-α-cyano-3-phenoxybenzyl (1RS)cis, trans-3-(2-chloro-3,3,3-trifluoropropenyl)-2,2-dimethylcyclopropanecarboxylate and 4-methyl-2,3,5,6-tetrafluorobenzyl 3-(2-chloro-3,3,3-trifluoro-1-propen-1-yl)-2,2-dimethylcyclopropanecarboxylate; such compounds as 2-tertbutylimino-3-isopropyl-5-phenyl-3,4,5,6-tetrahydro-2H-1,3,5-thiazine-4-one, trans-5-(4-chlorophenyl)-N-cyclohexyl-4-methyl-2-oxothiazolidinone-3-carboxamide, N-methyl-bis(2,4-xylyliminomethyl)amine and N'-(4-chloro-o-tolyl)-N,N-dimethylformamide; juvenile hormonelike compounds such as isopropyl (2E, 4E)-11-methoxy-3,7,11-trimethyl-2,4-dodecadienoate, and other compounds such as dinitro compounds, organic sulfur compounds, urea compounds and triazine compounds. Moreover, agricultural chemical microorganisms, such as BT agents, and insect pathogenic virus inhibitors can be used in combination with other argicultural chemicals.

Examples of the fungicides are organic phosphoric compounds such as S-benzyl O,O-diisopropyl phosphorothioate, O-ethyl S,S-diphenyl phosphorodithioate and aluminum ethyl hydrogen phosphate; organic chlorine compounds such as 4,5,6,7-tetrachlorophthalide and tetrachloroisophthalonitrile; dithiocarbamate compounds such as manganese ethylenebis(dithiocarbamate) polymer, zinc ethylenebis(dithiocarbamate) polymer, zinc-manganese ethylenebis(dithiocarbamate) compounds, zinc bis(dimethyldithiocarbamate) and zinc propylenebis(dithiocarbamate) polymer; N-halogenothioalkyl compounds such as 3a,4,7,7a-tetrahydro-N-(trichloromethanesulfenyl)phthalimide, 3a,4,7,7a-tetrahydro-N-(1,1,2,2,-tetrachloroethanesulfenyl)phthalimide and N-(trichloromethylsulfenyl)-phthalimide; dicarboxyimide compounds such as 3-(3,5-dichlorophenyl)-N-isopropyl-2,4-dioxoimidazolidine-1-carboxamide, (RS)-3-(3,5-dichlorophenyl)-5-methyl-5-vinyl-1,3-oxazolidine-2,4-dione and N-(3,5-dichlorophenyl)-1,2-dimethylcyclopropane-1,2-dicarboximide; benzimidazole compounds such as methyl-1-(butylcarbamoyl)benzimidazol-2-yl carbamate and dimethyl 4,4'-(o-phenylene)-bis(3-thioallophanate); azole compounds such as 1-(4-chlorophenoxy)-3,3-dimethyl-1-(1H-1,2,4-triazol-1-yl)butanone, 1-(biphenyl-4-yloxy)-3,3-dimethyl-1-(1H-1,2,4-triazol-1-yl)butane-2ol, 1-[N-(4-chloro-2-trifluoromethylphenyl)-2-propoxyacetoimidoyl-]imidazole, 1-[2-(2,4-dichlorophenyl)-4-ethyl-1,3-dioxolane-2-ylmethyl]-1H-1,2,4-triazole, 1-[2-(2,4-dichlorophenyl)-4-propyl-1,3-dioxalan-2-ylmethyl]-1H-1,2,4-triazole and 1-[2-(2,4-dichlorophenyl)pentyl]-1H-1,2,4-triazole; carbinol compounds such as 2,4'-dichloro-α-(pyrimidin-5-yl)benzhydryl alcohol and (±)2,4'-difluoro-α-(1H-1,2,4-triazole-1-ylmethyl)benzhydryl alcohol; benzanilide compounds such as 3'-isopropoxy-o-toluanilide and α,α,α-trifluoro-3'-isopropoxy-o-toluanilde; acylalanine compounds such as methyl N-(2-methoxyacetyl)-N-(2,6-xylyl)-DL-alaninate; pyridinamine compounds such as 3-chloro-N-(3-chloro-2,6-dinitro-4-α,α,α-trifluorotolyl)-5-trifluoromethyl-2-pyridinamine; and other compounds such as piperazine compounds, morpholine compounds, anthraquinone compounds, qunoxaline compounds, crotonic acid compounds, sulfenic acid compounds, urea compounds and antibiotic substances.

The active pesticidal ingredient is generally incorporated in the formulation an amount of 5 to 80 percent, preferably 5 to 40 percent, based on the total weight of the water-dispersible pesticide. A preferred amount of the organic solvent is 1/10 to 10 times the amount of the active pesticidal ingredient.

The water-dispersible pesticide formulation of the present invention can easily be prepared by utilizing existing equipment in the art. For example, powder components such as the carrier and surface active agent are charged into a ribbon type mixer or a screw type mixer, and a mixture formed by dissolving a part or all of the active pesticidal ingredient in the organic solvent is added and mixed with the carrier and the like at a temperature of from about 20° to about 100° C., more preferably from 30° to 80° C. To uniformly mix the components, the mixture is next disintegrated by passing it through a pulverizer such as a hammer mill, a pin mill or a jet-o-mizer. The pulverization product is typically uniformly mixed again with the ribbon type or screw type mixer to obtain the intended water-dispersible pesticide. If a high-speed rotary vane mixer such as a juice mixer type blender or a Henschel mixer is used, the mixing/pulverizing/mixing process as mentioned above can be accomplished in one apparatus merely by adjusting the stirring speed.

The water-dispersible pesticide formulations of the present invention will now be described with reference to the following examples. These examples are illustrative and should not be construed as limiting. Unless otherwise specified, all of "parts" and "percent" in these examples are by weight.

EXAMPLES

EXAMPLE 1

In 20 parts of N-methyl-2-pyrrolidone heated at 40° C. was dissolved 15 parts of 1-[3,5-dichloro-4-(1,1,2,2-tetrafluoroethoxy)phenyl]-3-(2,6-difluorobenzoyl)urea. Thereafter 25 parts of precipitated silica, 3 parts of polyoxyethylene alkylphenyl ether sulfate salt (Dixsol WR TM supplied by Dai-Ichi Kogyo), 2 parts of lignin-sulfonate salt (San-X P252 TM supplied by Sanyo Kokusaku Pulp), 10 parts of diatomaceous earth and 25 parts of clay were incorporated in the solution. The mixture was finely pulverized by a jet-o-mizer to obtain a wettable powder.

EXAMPLE 2

In 15 parts of cyclohexanone heated at 40° C. was dissolved 10 parts of 1-[3,5-dichloro-4-(1,1,2,2-tetrafluoroethoxy)phenyl]-3-(2,6-difluorobenzoyl)urea, and, thereafter, 20 parts of precipitated silica, 3 parts of polyoxyethylene nonylphenyl ether (Newcol 564 TM supplied by Nippon Nyukazai), 2 parts of San-X P252, 5 parts of soybean lecithin, 5 parts of diatomaceous earth and 40 parts of clay were incorporated in the solution. The mixture was finely pulverized by a jet-o-mizer to obtain a wettable powder.

EXAMPLE 3

Fifteen parts of 1-[3,5-dichloro-4-(1,1,2,2-tetrafluoroethoxy)phenyl]-3-(2,6-difluorobenzoyl)urea was dissolved in acetone in an amount 8 times the amount of the active ingredient, and 10 parts of precipitated silica, 4 parts of ammonium polyoxyethylene alkylaryl ether sulfate (Agrysol W-150 TM supplied by Kao), 2 parts of lignin-sulfonate salt (San-X P-201 TM supplied by Sanyo Kokusaku Pulp) and 69 parts of clay were incorporated in the solution. The acetone was removed by volatilization in a rotary evaporator and the residue was uniformly mixed and pulverized by a hammer type pulverizer to obtain a wettable powder.

EXAMPLE 4

Fifteen parts of 1-[3,5-dichloro-4-(1,1,2,2-tetrafluoroethoxy)phenyl]-3-(2,6-difluorobenzoyl)urea was dissolved in dichloromethane in an amount 10 times the amount of the active ingredient, and, thereafter, 10 parts of precipitated silica, 4 parts of alkylaryl sulfonate (Lunox P-65-L TM supplied by Toho Kagaku), 2 parts of San-X P201, and 69 parts of clay were incorporated in the solution. Dichloromethane was volatilized by a rotary evaporator and the residue was uniformly mixed and pulverized by a hammer type pulverizer to obtained a wettable powder.

EXAMPLE 5

In 15 parts of N-methyl-2-pyrrolidone was dissolved 10 parts of 1-[3,5-dichloro-4-(3-chloro-5-trifluoromethyl-2-pyridyloxy)phenyl]-3-(2,6-difluorobenzoyl)urea at an elevated temperature of 40° C., and, thereafter, 15 parts of precipitated silica, 4 parts of naphthalene-sulfonate/formalin condensate (Demoul N TM supplied by Kao), 3 parts of polyoxyethylene nonylphenyl ether (New Calgen 405H TM supplied by Takemoto Yushi), 20 parts of diatomaceous earth and 33 parts of clay were incorporated and uniformly mixed into the solution. The blend was pulverized and mixed by a high-speed rotary vane type mixer (juice mixer type blender) to obtain a wettable powder.

EXAMPLE 6

Ten parts of 1-[3,5-dichloro-4-(3-chloro-5-trifluoromethyl-2-pyridyloxy)phenyl]-3-(2,6-difluorobenzoyl)urea was dissolved in methyl alcohol in an amount 6 times the amount of the active ingredient at an elevated temperature of 40° C., and, thereafter, 10 parts of precipitated silica, 3 parts of an anionic surface active agent (Detergent N06F TM supplied by Kao), 2 parts of San-X P252, 10 parts of diatomaceous earth and 65 parts of clay were incorporated in the solution. Methyl alcohol was volatilized by a rotary evaporator, and the residue was uniformly mixed and pulverized and by a high-speed rotary vane type mixer (juice mixer type blender) to obtain a wettable powder.

EXAMPLE 7

Ten parts of 1-(3,5-dichloro-2,4-difluorophenyl)-3-(2,6-difluorobenzoyl)urea was dissolved in chloroform in an amount 8 times the amount of the active ingredient at an elevated temperature of 40° C., and, thereafter, 10 parts of precipitated silica, 4 parts of naphthalene-sulfonate/formalin condensate (Demoul T TM supplied by Kao), 3 parts of phenylphenol sulfonate/formalin condensate (New Calgen 9131 TM supplied by Takemoto Yushi), 20 parts of diatomaceous earth and 53 parts of clay were incorporated into the solution. Chloroform was volatilized by a rotary evaporator and the residue was uniformly mixed and finely pulverized by a jet-o-mizer to obtain a wettable powder.

EXAMPLE 8

In 20 parts of dimethylformamide was dissolved 10 parts of 1-(3,5-dichloro-2,4-difluorophenyl)-3-(2,6-difluorobenzoyl)urea at an elevated temperature of 50° C. and 25 parts of precipitated silica, 4 parts of polyoxyethylene alkylphenyl ether sulfate salt (Dixsol W-66 TM supplied by Dai-Ichi Kogyo), 2 parts of San-X P252, 10 parts of diatomaceous earth and 29 parts of clay were incorporated and uniformly mixed into the solution. The mixture was finely pulverized by a jet-o-mizer to obtained a wettable powder.

EXAMPLE 9

Thirty parts of 1-(4-chlorophenyl)-3-(2,6-difluorobenzoyl)urea was partially dissolved in 20 parts of N-methyl-2-pyrrolidone at an elevated temperature of 40° C., and, thereafter, 20 parts of precipitated silica, 4 parts of sodium lauryl sulfate (Emal 10 powder TM supplied by Kao), 2 parts of special aromatic sulfonic acid/formalin condensate (Demoul TM MS supplied by Kao), 10 parts of diatomaceous earth and 14 parts of clay were incorporated and uniformly mixed into the solution. The mixture was pulverized by a hammer type pulverizer to obtain a wettable powder.

EXAMPLE 10

Forty parts of 1-(4-trifluoromethoxyphenyl)-3-(2-chlorobenzoyl)urea was partially dissolved in dichloromethane in an amount 5 times the amount of the active ingredient at an elevated temperature of 40° C., and, thereafter, 5 parts of precipitated silica, 3 parts of alkyl sulfate (Sorpol 8070 TM supplied by Toho Kogaku), 2 parts of San-X P201 and 50 parts of clay were incorporated in the solution. Dichloromethane was removed by volatilization in a rotary evaporator. The residue was uniformly mixed and the mixture was pulverized by a hammer type pulverizer to obtain a wettable powder.

EXAMPLE 11

In 25 parts of N-methyl-2-pyrrolidone was dissolved 10 parts of 1-[2-fluoro-4-(2-chloro-4-trifluoromethylphenoxy)phenyl]-3-(2,6-difluorobenzoyl)urea at an elevated temperature of 40° C., and, thereafter, 25 parts of precipitated silica, 4 parts of polyoxyethylene alkylphenyl ether ester salt (Dixsol WA TM supplied by Dai-Ichi Kogyo), 2 parts of naphthalene-sulfonic acid/formalin condensate (Demoul N TM supplied by Kao), 4 parts of soybean lecithin and 30 parts of diatomaceous earth were incorporated and uniformly mixed into the solution. The mixture was finely pulverized by a jet-o-mizer to obtain a wettable powder.

EXAMPLE 12

Effect on Diamondback Moth

Each of the wettable powders obtained in Examples 1, 2, 3 and 4 was diluted with water. Cabbage leaves were immersed in each chemical liquid, and the leaves were air-dried and placed in an individual polyvinyl chloride resin cups. Then, 4th-instar larvae of diamondback moth were set free in each cup. The cups were placed in a chamber maintained at a temperature of 25° C. and a relative humidity of 65 percent, and after 10 days, the number of insects emerging was examined. Five larvae were set free in each test cup, and 20 larvae were tested with respect to each concentration.

The results are shown in Table 1.

TABLE 1

| Wettable Powder Tested | Concentration (ppm) | Number of Emerging Insects |
| --- | --- | --- |
| wettable powder obtained in Example 1 | 5 | 0 |
|  | 0.5 | 0 |
| wettable powder obtained in Example 2 | 5 | 0 |
|  | 0.5 | 0 |
| wettable powder obtained in Example 3 | 5 | 0 |
|  | 0.5 | 1 |
| wettable powder obtained in Example 4 | 5 | 0 |
|  | 0.5 | 1 |
| untreated control section | — | 20 |

EXAMPLE 13

Effect on Tobacco Cutworm

Each of the wettable powders obtained in Examples 5, 6, 7 and 8 was diluted with water. Cabbage leaves were individually immersed for 60 seconds in each chemical liquid, air-dried and placed in a polyvinyl chloride resin cup. Five 3rd-instar larvae of tobacco cutworm were set free in each cup, and the cups were placed in a chamber maintained at a temperature of 25° C. and a relative humidity of 65 percent. After 5 days, the control in percent was recorded.

The results are shown in Table 2.

TABLE 2

| Wettable Powder Tested | Concentration (ppm) | Control (%) after 5 Days |
| --- | --- | --- |
| wettable powder obtained in Example 5 | 5 | 100 |
|  | 0.5 | 90 |
| wettable powder obtained in Example 6 | 5 | 100 |
|  | 0.5 | 85 |
| wettable powder obtained in Example 7 | 5 | 100 |
|  | 0.5 | 85 |

TABLE 2-continued

| Wettable Powder Tested | Concentration (ppm) | Control (%) after 5 Days |
|---|---|---|
| wettable powder obtained in Example 8 | 5 | 100 |
| | 0.5 | 85 |
| untreated control section | — | 0 |

EXAMPLE 14

Effect on Rice Stem Borer

Each of the wettable powders obtained in Examples 9, 10 and 11 was diluted with water. Rice seedlings were immersed for 60 seconds in each chemical liquid, air-dried, and placed in a polyvinyl chloride resin cup. Five 3rd-instar larvae were set free in each cup, and the cups were preserved in a chamber maintained at a temperature of 25° C. and a relative humidity of 65 percent. After 5 days, the control percent was recorded.

The results are shown in Table 3.

TABLE 3

| Wettable Powder Tested | Concentration (ppm) | Control (%) after 5 Days |
|---|---|---|
| wettable powder obtained in Example 9 | 10 | 100 |
| | 1 | 75 |
| wettable powder obtained in Example 10 | 10 | 100 |
| | 1 | 80 |
| wettable powder obtained in Example 11 | 10 | 100 |
| | 1 | 70 |
| untreated control section | — | 0 |

What is claimed is:

1. A process for preparing a highly active water-dispersible pesticide which comprises dissolving at least a part of an insecticidally effective benzoyl phenyl urea series compound represented by the following formula:

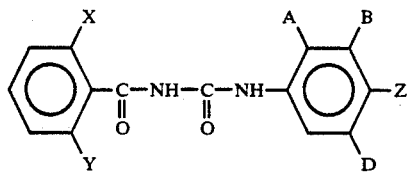

wherein:
X represents Cl, F, Br, or $CF_3$;
Y represents H, Cl, F, or Br;
Z represents Cl, F, Br, CN, $CF_3$, $CHF_2$, $OCF_3$, $OCF_2H$, $SCF_3$, $OCF_2CHF_2$, $OCF_2CHFCl$, $OCF_2CHFBr$, or a substituent of the formula

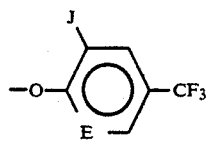

wherein:
E represents CH or N;
J represents H, Cl, F, or Br; and
A, B, and D each independently represent H, $CH_3$, F, Cl, or Br in an organic solvent to obtain a mixture comprising a solution containing the insecticidal compound, combining the so obtained mixture with a carrier material, and pulverizing the combined mixture and carrier material into a wettable powder.

2. A process of claim 1 wherein the mixing and pulverizing steps are conducted at temperatures of from about 20° to about 100° C.

3. A process of claim 1 wherein the insecticidal compound and the solvent are mixed in quantities which provide a weight ratio of active ingredient to solvent of from 0.01 to 100.

4. A process of claim 1 wherein the benzoyl phenyl urea series compound is selected from 1-[3,5-dichloro-4-(1,1,2,2-tetrafluoroethoxy)phenyl]-3-(2,6-difluorobenzoyl)urea, 1-[3,5-dichloro-4-(3-chloro-5-trifluoromethyl-2-pyridyloxyl)phenyl]-3-(2,6-difluorobenzoyl)urea, 1-(3,5-dichloro-2,4-difluorophenyl)-3-(2,6-difluorobenzoyl)urea, 1-(4-chlorophenyl)-3-(2,6-difluorobenzoyl)urea, 1-(4-(trifluoromethoxyphenyl)-3-(2-chlorobenzoyl)urea and 1-[2-fluoro-4-(2-chloro-4-trifluoromethylphenoxy)phenyl]-3-(2,6-difluorobenzoyl)urea.

5. A process of claim 1 wherein the carrier material is a plant powder, a mineral powder, an inorganic compound, an organic compound or a mixture thereof.

6. A process of claim 5 wherein the carrier material is a soybean powder, wheat flour, diatomaceous earth, apatite, gypsum, talc, bentonite, clay, kaolin, calcium carbonate, montmorillonite, feldspar, quartz, sodium benzoate, urea, Glauber salt, alumina, precipitated silica or a mixture thereof.

7. A process of claim 1 wherein the solvent is selected from alcohols, ketones, ethers, aliphatic hydrocarbons, aromatic hydrocarbons, halogenated hydrocarbons, esters, nitriles, highly polar solvents, epoxidized plant oils, epoxidized coconut oil and mixtures thereof.

8. A process of claim 7 wherein the solvent is acetone, dichloromethane, chloroform, methyl alcohol, N-methyl-2-pyrrolidone, cyclohexanone or dimethylformamide.

9. A process of claim 1 which further comprises adding a surface active agent to the mixture of the insecticidal compound and carrier material.

10. A process of claim 9 wherein the surface active agent is selected from a sulfate or sulfonate type anionic surface active agent, polyoxyethylene type non-ionic surface active agent, a water-soluble polymeric substance and a polyoxyethylene ether phosphate type anionic surface active agent.

11. A process of claim 1 which further comprises adding an adjuvant selected from a spreading agent, an emulsifier, a decomposition-preventing agent, a solidification-preventing agent, an activity-increasing agent and a mixture thereof to the mixture of the insecticidal compound and carrier material.

12. A process of claim 1 which further comprises adding an agricultural chemical selected from an insecticide, an acaricide, a nematicide, a fungicide, an antiviral agent, an insect attractant, a herbicide, a plant growth regulator and a mixture thereof to the mixture of the insecticidal compound and carrier material.

13. A process of claim 9 wherein the insecticidal compound is 1-[3,5-dichloro-4-(1,1,2,2-tetrafluoroethoxy)phenyl]-3-(2,6-difluorobenzoyl)urea, the carrier is precipitated silica and the surface active agent is a sulfate type anionic surface active agent.

* * * * *